United States Patent
Krainer et al.

(10) Patent No.: US 8,088,937 B2
(45) Date of Patent: *Jan. 3, 2012

(54) ALKYLTIN SULFANYL DIESTER THIOLS

(75) Inventors: Edward Krainer, New Fairfield, CT (US); Peter Frenkel, Danbury, CT (US)

(73) Assignee: Galata Chemicals, LLC, Southbury, CT (US)

( * ) Notice: Subject to any disclaimer, the term of this patent is extended or adjusted under 35 U.S.C. 154(b) by 15 days.

This patent is subject to a terminal disclaimer.

(21) Appl. No.: 12/832,701

(22) Filed: Jul. 8, 2010

(65) Prior Publication Data

US 2010/0298589 A1    Nov. 25, 2010

Related U.S. Application Data

(62) Division of application No. 11/634,474, filed on Dec. 5, 2006, now Pat. No. 7,781,504.

(51) Int. Cl.
    *C07F 15/00*      (2006.01)
    *C07F 7/22*      (2006.01)

(52) U.S. Cl. .............. 556/41; 556/93; 556/94; 524/180; 524/567; 524/568

(58) Field of Classification Search ................. 524/180, 524/568, 567; 556/41, 93, 94
See application file for complete search history.

(56) References Cited

U.S. PATENT DOCUMENTS

| | | | |
|---|---|---|---|
| 3,115,509 A | 12/1963 | Mack | |
| 3,539,529 A | 11/1970 | Kawakami et al. | |
| 3,682,992 A | 8/1972 | Kawakami et al. | |
| 3,979,359 A | 9/1976 | Kugele et al. | |
| 7,767,740 B2 | 8/2010 | Krainer et al. | |

*Primary Examiner* — Peter D Mulcahy
(74) *Attorney, Agent, or Firm* — Dilworth IP, LLC

(57) ABSTRACT

Disclosed herein are compounds of the formula:

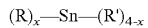

wherein:
  R is alkyl;
  R' is a moiety selected from the group consisting of:

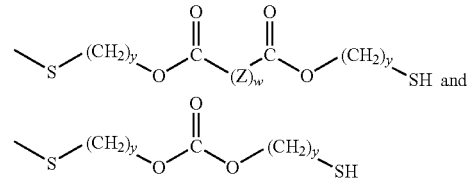

w is 0 or 1;
x is 1 or 2;
y is 1, 2, 3, or 4; and
Z is a linear, branched, cyclic, or aromatic hydrocarbon.
These compounds are excellent stabilizers for halogen-containing resins, such as PVC.

9 Claims, No Drawings

ALKYLTIN SULFANYL DIESTER THIOLS

CROSS-REFERENCE TO RELATED APPLICATIONS

This application is a Division of Ser. No. 11/634,474, filed Dec. 5, 2006.

BACKGROUND OF THE INVENTION

1. Field of the Invention

The present invention relates to alkyltin thermal stabilizers for halogen-containing resin compositions. More particularly, the present invention relates to alkyltin sulfanyl diester thiols that have from one to three terminal thiol groups and are suitable for thermal stabilization of halogen-containing resins, e.g., PVC, compositions.

2. Description of Related Art

The conventional commercially available organotin stabilizers, such as alkyltin bis- and/or tris-(mercaptopropionates) and/or (thioglycolates) are prepared using thioacids (such as mercaptoacetic and mercaptopropionic), an aliphatic alcohol and mono- or di-alkyltin chloride, where all SH-group are reacted with the alkyltin chloride (alkyl groups are methyl, n-butyl or octyl). Alkyltin oxides (especially butyltin oxide) are also known to be used as a source of tin.

U.S. patent application Ser. No. 11/124,464, filed May 5, 2005, discloses an alkyltin compound of a specified formula that is said to have utility as a stabilizer for a halogen-containing resin. The alkyltin compound has from one to three terminal thiol groups. The heat stabilizing performances of dimethyltin bis(1,2-ethane dithioglycolate), monomethyltin tris(1,2-ethanedithioglycolate), dimethyltin bis(1,2-ethane dimercaptopropionate), monomethyltin tris(1,2-ethanedimercaptopropionate) and mixtures thereof are specifically disclosed.

U.S. Pat. No. 3,115,509 (see also GB 866,484) generically discloses condensation products of organotin compounds with dimercaptoacid esters of organic thiols. These condensation products have the general formula

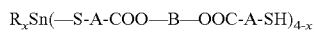

wherein x is 1, 2, or 3, R is a univalent organic radical, A is a hydrocarbon group, B is a hydrocarbon radical, and the sum of the carbon atoms of A and B is preferably no more than 25, and are said to stabilize vinyl resins against the degradative effects of both heat and light.

U.S. Pat. Nos. 3,539,529 and 3,682,992 disclose compositions and a stabilized polyvinyl chloride resin composition comprising essentially, in a predominant amount, a polyvinyl chloride resin and, in a small amount, at least one boron-containing organotin compound having the formula

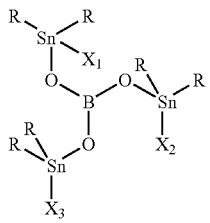

wherein R is a member selected from the group consisting of alkyl, alkenyl, aralkyl, alkylaryl and aryl; $X_1$ is a member selected from the group consisting of the residues of mono-mercapto compounds, dimercapto compounds and polymercapto compounds, said residues containing at least one free sulfhydryl radical; and $X_2$ and $X_3$ are members selected from the group consisting of hydroxyl, the same residues as $X_1$, the residues of carboxylic acids and maleic acid monoesters, and the residues of mercapto compounds containing no free sulfhydryl radical.

The disclosures of the foregoing are incorporated herein by reference in their entirety.

Non-thiol terminated alkyltin stabilizers are also known. For example, dimethyltin bis S,S (2-ethylhexanol thioglycolate) and di-n-butyl bis S,S (2-ethylhexanol thiolglycolate) are both commercially available. One of the most effective thermal stabilizers is a blend of dimethyltin bis S,S (2-ethylhexanol thioglycolate) and methyltin tris S,S,S (2-ethylhexanol thioglycolate), which is also commercially available.

SUMMARY OF THE INVENTION

As noted above, the present invention relates to alkyltin thermal stabilizers for halogen-containing resin compositions. More particularly, the present invention relates to alkyltin sulfanyl diester thiols that have from one to three terminal thiol groups and are suitable for thermal stabilization of halogen-containing resin, e.g., PVC, compositions.

More particularly, the present invention is directed to a compound of the formula:

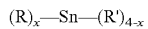

wherein:
R is alkyl;
R' is a moiety selected from the group consisting of:

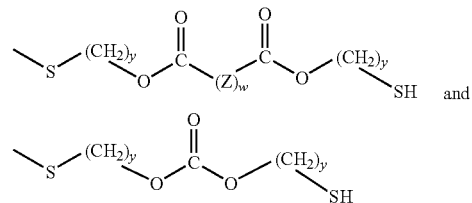

w is 0 or 1;
x is 1 or 2;
y is 1, 2, 3, or 4; and
Z is a hydrocarbon, which may be linear, branched, cyclic, or aromatic.

In another aspect, the present invention is directed to a composition comprising:
(A) a halogen-containing resin; and
(B) an amount effective to stabilize the halogen-containing resin against elevated temperatures, UV light, oxidation, and high shear forces of at least one compound of the formula:

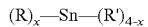

wherein:
R is alkyl;
R' is a moiety selected from the group consisting of:

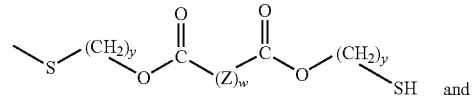

-continued

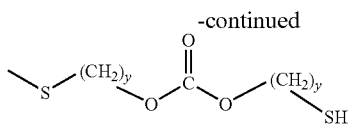

w is 0 or 1;
x is 1 or 2;
y is 1, 2, 3, or 4; and
Z is a hydrocarbon, which may be linear, branched, cyclic, or aromatic.

In still another aspect, the present invention is directed to a method for stabilizing a halogen-containing resin against elevated temperatures, UV light, oxidation, and high shear forces comprising adding to said halogen-containing resin a stabilizing amount of at least one compound of the formula:

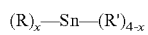

wherein:
R is alkyl;
R' is a moiety selected from the group consisting of:

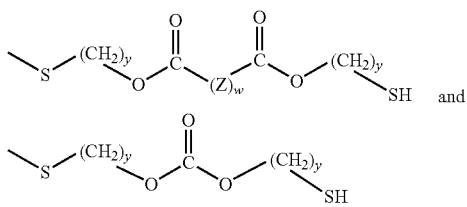

w is 0 or 1;
x is 1 or 2;
y is 1, 2, 3, or 4; and
Z is a hydrocarbon, which may be linear, branched, cyclic, or aromatic.

In yet another aspect, the present invention is directed to a method for the preparation of the above-described compound comprising:

(A) esterifying a mercaptoalcohol with a diacid (or an anhydride or an ester of the diacid) or a diester carbonate in a molar ratio of 2:1 in the presence of a suitable catalyst to produce a dithiol ester; and (B) reacting said dithiol ester with a dialkyltin or monoalkyltin reactant at the atom ratio of S:Sn>2, It will be understood that in the above formulae, where w is 0, the Z group is not present and the two carbonyl groups are directly attached to one another.

DESCRIPTION OF THE PREFERRED EMBODIMENTS

The compounds of the present invention are of the formula:

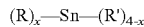

In the formula, R is preferably alkyl of from 1 to 12 carbon atoms, e.g., methyl, ethyl, propyl, butyl, pentyl, hexyl, heptyl, octyl, nonyl, decyl, undecyl, dodecyl, isomers of the foregoing, e.g., ethylhexyl, t-butyl, and the like, and mixtures thereof. More preferably, R is alkyl of from one to eight carbon atoms; most preferably, methyl, butyl, or octyl.

R' is a moiety selected from the group consisting of:

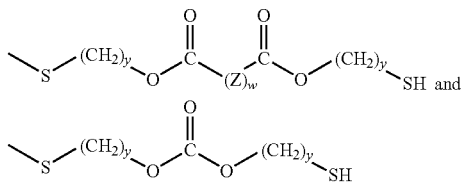

w is 0 or 1;
x is 1 or 2;
y is 1, 2, 3, or 4; and
Z is a hydrocarbon, which may be linear, branched, cyclic, or aromatic. Where Z is present, i.e., when w equals 1, it preferably comprises from 1 to 12 carbon atoms, e.g., straight or branched-chain alkylene, straight or branched-chain alkenylene, cyclopentylene, cyclohexylene, norbornylene, phenylene, naphthylene, and the like, any of which can, if desired, be substituted with any group or groups that will not significantly diminish the stabilizing properties of the overall compound. More preferably, Z, when present, comprises from one to eight carbon atoms, most preferably from two to four carbon atoms.

Alkyltin compounds that are particularly preferred in the practice of the present invention include, but are not limited to, dimethyltin bis[di(2-mercaptoethyl) succinate], monomethyltin tris[di(2-mercaptoethyl) succinate], dimethyltin bis[di(2-mercaptoethyl) adipate], monomethyltin tris[di(2-mercaptoethyl) adipate], dibutyltin bis[di(2-mercaptoethyl) succinate], monobutyltin tris[di(2-mercaptoethyl) succinate], dibutyltin bis[di(2-mercaptoethyl)adipate], monobutyltin tris[di(2-mercaptoethyl) adipate], dioctyltin bis[di(2-mercaptoethyl) succinate], monooctyltin tris[di(2-mercaptoethyl) succinate], dioctyltin bis [di(2-mercaptoethyl)adipate], monooctyltin tris[di(2-mercaptoethyl)adipate], monomethyltin tris[di(2-mercaptoethyl) carbonate], dimethyltin bis[di(2-mercaptoethyl) carbonate], monobutyltin tris[di(2-mercaptoethyl) carbonate], dibutyltinbis[di(2-mercaptoethyl) carbonate], monooctyltin tris[di(2-mercaptoethyl)carbonate], dioctyltin bis[di(2-mercaptoethyl)carbonate], monomethyltin tris[di(3-mercaptopropyl)carbonate], dimethyltin bis[di(3-mercaptopropyl)carbonate], dimethyltin bis[di(4-mercaptobutyl)carbonate], and mixtures thereof.

These organotin compounds may be generally described as condensation products of organotin derivatives (such as alkyltin oxides and alkyltin chlorides) and bis(mercaptoalkyl esters) of dibasic organic acids or of carbonic acid. The mercaptoalkyl esters can be obtained via reactions of dibasic acids or their anhydrides or their alkylesters with mercaptoalcohols. The bis(mercaptoalkyl) carbonates can be prepared from mercaptoalcohol and a dialkyl carbonate.

Those of ordinary skill in the art will recognize that the alkyltinsulfanyl diester thiol compounds of the present invention can be prepared via several synthetic routes. In a preferred embodiment, these alkyltin compounds may be conveniently synthesized using a two-reaction procedure that employs readily available reactants. First, a dithiol ester is prepared by esterification of a mercaptoalcohol with a diacid (or its anhydride, or its ester) in a molar ratio of 2:1 in the presence of a suitable catalyst. Suitable mercaptoalcohols include 2-mercaptoethanol, mercaptopropanol, and mercaptobutanol. Appropriate diacids and their anhydrides include succinic, adipic, maleic, fumaric, malonic, oxalic, glutaric, phthalic, isophthalic, and terephthalic. Suitable esters are mono and dialkyl esters, such as methyl, ethyl, n-propyl, iso-propyl, n-butyl, sec-butyl, tert-butyl, and the like, and their corresponding hydroxy and alkyloxy and thio derivatives. The catalysts include, but are not limited to, p-toluene sulfonic acid, methane sulfonic acid, sulfuric acid, and titanium(1V) isopropoxide.

The esterification reaction may be performed with or without a solvent at an appropriate temperature, for example, 60-150° C. Water or alcohol formed during the reaction is removed by conventional methods (e.g., distillation) that can be carried out under vacuum or at ambient pressure.

The resulting dithiol ester may be neutralized with an appropriate base such as sodium bicarbonate or potassium carbonate, purified by filtering salt residues out or by washing with water, and stripped under 3 mm Hg vacuum to remove moisture, preferably at an elevated temperature such as, for example, 60-80° C.

In the second stage of the synthesis, the dithiol ester is reacted with an appropriate reactant comprising tin, for example an alkyltin chloride or alkyltin oxide, at an atom ratio of S:Sn>2. The resulting alkyltin compound thus contains both Sn—S bonds and free, terminal thiol groups.

The alkyltin compounds of the present invention impart superior thermal stability to halogen-containing resins. The halogen of such resins can be fluorine, chlorine, bromine, iodine, or mixtures thereof. The polymer that is stabilized by the compounds of the present invention is preferably PVC.

The PVC used can be obtained via polymerization in bulk or in suspension, or in emulsion, or in micro suspension, or in suspended emulsion.

As employed herein, the terms "poly(vinyl chloride)" and "PVC" are intended to include both homopolymers and copolymers of vinyl chloride, i.e., vinyl resins containing vinyl chloride units in their structure, e.g., copolymers of vinyl chloride and vinyl esters of aliphatic acids, in particular vinyl acetate; copolymers of vinyl chloride with esters of acrylic and methacrylic acid and with acrylonitrile; copolymers of vinyl chloride with diene compounds and unsaturated dicarboxylic acids or anhydrides thereof, such as copolymers of vinyl chloride with diethyl maleate, diethyl fumarate or maleic anhydride; post-chlorinated polymers and copolymers of vinyl chloride; copolymers of vinyl chloride and vinylidene chloride with unsaturated aldehydes, ketones and others, such as acrolein, crotonaldehyde, vinyl methyl ketone, vinyl methyl ether, vinyl isobutyl ether, and the like.

The terms "poly(vinyl chloride)" and "PVC" as employed herein are also intended to include graft polymers of PVC with EVA, ABS, and MBS. Preferred substrates are also mixtures of the above-mentioned homopolymers and copolymers, in particular vinyl chloride liomopolymers, with other thermoplastic and/or elastomeric polymers, in particular blends with ABS, MBS, NBR, SAN, EVA, CPE, MBAS, PMA, PMMA, EPDM, and polylactones.

Vinyl acetate, vinylidene dichloride, acrylonitrile, chlorofluoroethylene and/or the esters of acrylic, fumaric, maleic and/or itaconic acids may be mentioned as preferred examples of monomers that are copolymerizable with vinyl chloride. In addition, polyvinyl chloride can be chlorinated having a chlorine content of up to 70% by weight. This invention applies particularly to the vinyl chloride homopolymers.

Within the scope of this invention, PVC will also be understood to include recyclates of halogen-containing polymers that have suffered damage by processing, use or storage.

An effective amount of the alkyltin compound of the present invention is an amount that makes the halogen-containing resin more resistant to discoloration than the resin per se. Generally, an effective amount will range from about 0.5 to about 1.50 parts of the stabilizer per hundred parts resin and will depend on the specific resin and alkyltin compound, as well as the degree of thermal stabilization desired. A preferred amount of alkyltin compound is from about 0.8 to about 1.2 parts of the stabilizer per hundred parts resin.

The alkyltin compound may be added to the halogen-containing resin using techniques and apparatus well known to those of ordinary skill in this art. Generally, the resin may be mixed with the stabilizer in a high-speed mixer for 30-90 seconds to thoroughly disperse the alkyltin compound throughout the resin.

The halogen-containing resin may also contain known additives, as long as their presence does not materially degrade the thermal stability imparted by the alkyltin compounds of the present invention. Such additives include, without limitation, lubricants, fillers, pigments, flame retardants, UV absorbers, impact modifiers, and processing aids. These additives may be added to the resin using techniques and apparatus well known to those of ordinary skill in this art.

Suitable lubricants include calcium stearate, montan wax, fatty acid esters, polyethylene waxes, chlorinated hydrocarbons, glycerol esters, and combinations thereof. Suitable fillers include titanium oxide, calcium carbonate, kaolin, glass beads, glass fibers, talc, wood flour, and mixtures thereof.

Suitable pigments include azo pigments, phthalocyanine pigments, quinacridone pigments, perylene pigments, diketopyrrolopyrrole pigments and anthraquinone pigments. Suitable flame retardants include antimony oxide, molybdates, borates, and hydroxystannates.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

Example 1

Synthesis of Dimethyltin
bis[di-(2-Mereaptoethyl)Succinate] from Succinic
Anhydride Succinic anhydride (80.56 grams) was reacted with 137.5 grams of 2-mercaptoethanol in the presence of 0.56 gram of methanesulfonic acid (MSA) at 60° C. and 30 mm Hg. Over a period of 5.5 hours, the reaction temperature was increased to 110° C., and a mixture of water with 2-mercaptoethanol was collected. After cooling down, the batch was neutralized with a 7% aqueous solution of $NaHCO_3$ and filtered to yield 176.75 grams of the clear product [di(2-mercaptoethyl)succinate] upon drying at 65° C. and 3 mm Hg. The mercaptan value by iodine titration was 26.05%.

Seventy-five grams of the di(2-mercaptoethyl)succinate was reacted with 30.75 grams of dimethyltin dichloride dissolved in 30 ml of water. The reaction mixture was neutralized at 80° C. to pH 6.5 using an ammonium hydroxide solution. The crude product was separated from the aqueous phase and stripped at 55° C. and 3 mm Hg for two hours using a Buchi Rotavapor R-114 evaporator. The product was filtered to remove traces of residual salts to yield 88.91 grams of the clear product. Analysis: sulfur found 19.88%, calculated 20.74; tin found 17.94%, calculated 18.65%.

Example 2

Synthesis of Monomethyltin tris[di-(2-Mercaptoethyl Succinate]

The di(2-mercaptoethyl) succinate (75 grams) was reacted with 23.26 grams of monomethyltin chloride dissolved in 30 ml of water. The reaction mixture was neutralized at 80° C. to pH 6.5 using an ammonium hydroxide solution. The crude product was separated from the aqueous phase and stripped at 55° C. and 3 mm Hg for two hours using a Buchi Rotavapor R-114 evaporator. The product was filtered to remove traces of residual salts to yield 79.09 grams of the clear product. Analysis: sulfur found 22.68%, calculated 22.72%; tin found 13.22%, calculated 14.06%.

Example 3

Synthesis of Dimethyltin bis[di-(2-Mercatoethyl)Adipate] from Adipic Acid

Adipic acid (116.91 grams) was reacted with 137.5 grams of 2-mercaptoethanol in the presence of 0.56 grain of methanesulfonic acid (MSA) at 60° C. under vacuum (30 mm Hg), distilling a mixture of water with 2-mercaptoethanol. After a period of 6.8 hours, the reaction mixture was cooled down to room temperature, washed with a 7% aqueous solution of $NaHCO_3$ and water, filtered, and dried under vacuum (3 mm HG. 60° C.) to yield 194.74 grams of the clear product di(2-mercaptoethyl) adipate. The mercaptan value by iodine titration was 20.6%.

The di(2-mercaptoethyl) adipate (94.85 grams) was reacted with 30.75 grams of dimethyltin dichloride dissolved in 35 ml of water. The reaction mixture was neutralized at 80° C. to pH 6.5 using an ammonium hydroxide solution. The crude product was separated from the aqueous phase and stripped at 55° C. and 3 mm Hg for two hours using a Buchi Rotavapor R-114 evaporator. The product was filtered to remove traces of residual salts to yield 98.0 grams of the clear product. Analysis: sulfur found 19.32%, calculated 19.02%; tin found 15.59%, calculated 17.10%.

Example 4

Evaluation of Color Stability

Rigid PVC formulations were prepared using the stabilizer of Example 1 and commercially available alkyltin stabilizers, such as dimethyltin-bis(2-ethyl hexylthioglycolate) (Mark 1982) and a blend of monomethyltin-tris(2-ethylhexylthioglycolate) with dimethyltin-bis(2-ethyl hexylthioglycolate) (Mark 1900). The stabilizers were applied at the same weight in the formulations. Each PVC compound test sample was placed into a Brabender mixer operated at 190° C. and 65 RPM. Sample chips were taken every three minutes. Fusion time was about the same for all samples.

Color stability was determined from sample chips using a Hunter Lab colorimeter measuring Yellowness Index (YI). The lower the YI, the less the amount of discoloration as a result of thermal decomposition, signifying superior thermal stabilization. Decomposition time was calculated from a torque/temperature chart as the time at which a torque of 2,300 meter*grams is reached. Longer times signify superior thermal stability. See Table 1.

TABLE 1

Effect of Heat Stabilizers on Yellowness Index and Decomposition Time of PVC

| Time (minutes) | Mark 1900 | Mark 1982 | Dimethyltin Succinate | 20/80 Mono/Dimethyltin succinate blend |
|---|---|---|---|---|
| 3 | 3.71 | 3.27 | 4.39 | 4.03 |
| 6 | 6.41 | 7.90 | 5.80 | 5.25 |
| 9 | 9.15 | 11.63 | 8.71 | 7.77 |
| 12 | 14.42 | 19.63 | 13.06 | 11.09 |
| 15 | 27.77 | 37.73 | 25.27 | 22.00 |
| Decomposition Time (minutes) | 18.0 | 17.5 | 23.5 | 20.3 |
| Stabilizer Tin content, % | 19.40 | 19.67 | 17.94 | 16.99 |
| Stabilizer added, phr | 1.2 | 1.2 | 1.2 | 1.2 |
| Tin amount added, phr | 0.23 | 0.24 | 0.22 | 0.20 |

"Initial color hold" refers to yellowing resistance during the first 3 to 10 minutes of the Brabender color stability test. Monoalkyltin stabilizers are known to provide an excellent initial color-hold.

"Long term heat stability" refers to yellowing resistance at times greater than 10 minutes in the Brabender color stability test. Dialkyltin stabilizers are known to provide superior long-term heat stability.

Blends of the monoalkyltin and dialkyltin moieties provide the most efficient balance of both initial color-hold and long-term heat stability. One such blend is a mixture of monomethyltin tris-(2-ethylhexylthioglycolate) and dimethyltin bis-(2-ethylhexylthioglycolate), which is commercially available from Chemtura Corporation under the trade designation Mark 1900.

Added at the same weight (and having a lower tin content), the dimethyltin bis[di(2-mercaptoethyl) succinate] stabilizer of the present invention achieved an initial color stability similar to or better than that of the Mark 1900 blend and Mark 1982, as measured by yellowness index (from 3 to about 10 minutes in the Brabender test; see Table 1.) In other words, the dimethyltin bis[di(2-mercaptoethyl) succinate] stabilizer was unexpectedly effective in initial color stabilization despite the absence of a monoalkyltin moiety in its composition. The mono/dimethyltin succinate blend was even more efficient than the dimethyltin succinate derivative. The dimethyltin bis[di(2-mercaptoethyl)succinate] stabilizer and its blend with the monomethyltin derivative also exhibited superior long-term heat stability in comparison to the Mark 1900 blend and Mark 1982, as demonstrated by the yellowness index curves from 10-15 minutes during the Brabender color stability test. The decomposition time results demonstrated the same trends (see Table 1).

In view of the many changes and modifications that can be made without departing from principles underlying the invention, reference should be made to the appended claims for an understanding of the scope of the protection to be afforded the invention.

What is claimed is:

1. A compound of the formula:

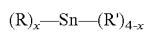

wherein:
R is alkyl;
R' is a moiety selected from the group consisting of:

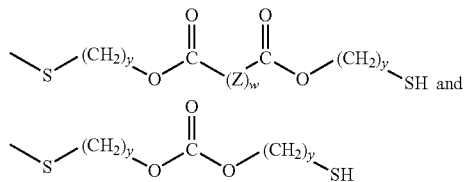

w is 0 or 1;
x is 1 or 2;
y is 1, 2, 3, or 4; and
Z is a linear, branched, cyclic, or aromatic hydrocarbon.

2. The compound of claim 1 wherein R is alkyl of from 1 to 12 carbon atoms.

3. The compound of claim 1 wherein R is alkyl of from one to eight carbon atoms.

4. The compound of claim 3 wherein R is methyl, butyl, or octyl.

5. The compound of claim 1 wherein the compound is selected from the group consisting of dimethyltin bis[di(2-mercaptoethyl) succinate], monomethyltin tris[di(2-mercaptoethyl) succinate], monomethyltin tris[di(2-mercaptoethyl) carbonate], dimethyltin bis[di(2-mercaptoethyl) carbonate], and mixtures thereof.

6. A method for the preparation of the alkyltin compound of claim 1 comprising:
(A) esterifying a mercaptoalcohol with a diacid (or an anhydride or an ester of the diacid) or a diester carbonate in a molar ratio of 2:1 in the presence of a suitable catalyst to produce a dithiol ester; and
(B) reacting said dithiol ester with a dialkyltin or monoalkyltin reactant at the atom ratio of S:Sn>2.

7. The method of claim 6 wherein the dialkyltin or monoalkyltin reactant is an alkyltin chloride or alkyltin oxide.

8. The method of claim 6 wherein the mercaptoalcohol is 2-mercaptoethanol.

9. The method of claim 6 wherein the diacid (or its anhydride, or its diester) is succinic or adipic.

* * * * *